United States Patent [19]

Fischer et al.

[11] Patent Number: 5,310,909

[45] Date of Patent: May 10, 1994

[54] PHOTOCHROMIC COMPOUNDS, A PROCESS FOR THEIR PREPARATION, AND THEIR USE

[75] Inventors: Evelyn Fischer, Weil am Rhein; Walter Fischer, Reinach; Jürgen Finter, Freiburg, all of Fed. Rep. of Germany; Kurt Meier, Therwil; Martin Roth, Giffers, both of Switzerland

[73] Assignee: Ciba-Geigy Corporation, Ardsley, N.Y.

[21] Appl. No.: 616,550

[22] Filed: Nov. 21, 1990

[30] Foreign Application Priority Data

Nov. 29, 1989 [CH] Switzerland .................. 4270/89

[51] Int. Cl.$^5$ .................. C07D 471/22; C07D 335/16; C07D 409/14; C07D 311/86
[52] U.S. Cl. .................. 546/41; 546/49; 546/62; 546/70; 546/103; 546/192; 546/207; 546/208; 546/209; 544/60; 544/145; 544/147; 544/148; 544/173; 544/174; 544/180; 548/364.4; 548/418; 548/423; 548/517; 548/518; 548/525; 549/23; 549/24; 549/27; 549/391; 549/25; 549/234; 549/235
[58] Field of Search .................. 549/391, 390, 27, 23, 549/24, 25, 234, 235; 546/103, 49, 62, 70, 192, 207, 208, 209; 430/270; 548/374, 418, 423, 517, 518, 525

[56] References Cited

U.S. PATENT DOCUMENTS

| | | | |
|---|---|---|---|
| 3,706,768 | 12/1972 | Boys et al. | 260/335 |
| 4,506,083 | 3/1985 | Kirta et al. | 549/27 |
| 4,681,950 | 7/1987 | Fischer et al. | 549/27 |
| 4,752,813 | 8/1978 | Shen et al. | 260/267 |

FOREIGN PATENT DOCUMENTS

919107 11/1954 Fed. Rep. of Germany.
2546822 4/1977 Fed. Rep. of Germany.

OTHER PUBLICATIONS

Derwent Abstract 83-744573/34 (1983).
B. K. Manukian, Helv. Chim. Acta, 59, 2609 (1976).
Chem. Abst. 53, 411c (1959).

*Primary Examiner*—C. Warren Ivy
*Assistant Examiner*—A. A. Owens
*Attorney, Agent, or Firm*—Luther A. R. Hall; Kevin T. Mansfield; George R. Dohmann

[57] ABSTRACT

Compounds of the formula I

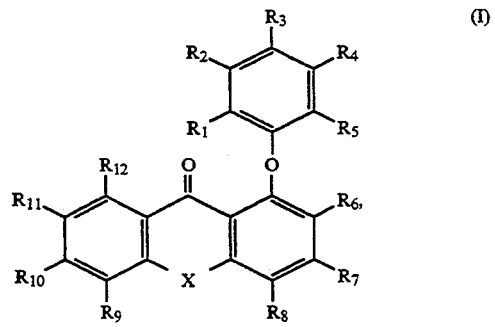

in which X is O, S, SO, SO$_2$ or NR$_{13}$, R$_{13}$ is, for example, methyl, and R$_1$ to R$_{12}$, independently of one another, are, for example, H, C$_1$–C$_{12}$alkyl, C$_1$–C$_{12}$Alkoxy, halogen or —CN. The compounds are photosensitive and photochromic and are suitable as photosensitizers and simultaneously as color indicators, and as photoswitchable color filters.

15 Claims, No Drawings

PHOTOCHROMIC COMPOUNDS, A PROCESS FOR THEIR PREPARATION, AND THEIR USE

The present invention relates to photochromic acridones, xanthones, thioxanthones, thioxanthone sulfoxides and thioxanthone sulfodioxides which are substituted in the 1-position by substituted or unsubstituted phenozy, to a process for their preparation, to a photosensitive composition, and to the use of these photochromic comounds as photosensitizers and colour indicators or as photoswitchable colour filters.

It is known that thioxanthones (See U.S. Pat. No. 4,506,083) are photoinitiators or photosensitizers for irradiation-sensitive polymerizable systems. B. K. Manukian, in Helv. Chim. Acta., Vol. 59, Fasc. 7 (1976), pp. 2609 to 2614, described 4-nitroacridones which are 1-substituted by substituted or unsubstituted phenoxy as dyes with good light-fastness properties, DE-A-919 107 describes 1-phenoxy-4-methylxanthen-9-one as an active ingredient for pharmaceuticals.

The prsent invention relates to compounds of the formula I

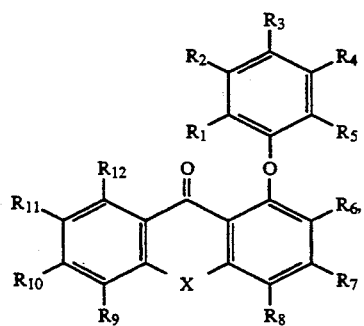

in which X is O, S, SO, $SO_2$ or $NR_{13}$, $R_1$ to $R_5$, independently of one another, are H, $C_1$-$C_{12}$alkyl, $C_1$-$C_{12}$alkoxy, $C_1$-$C_{12}$alkylthio, $C_1$-$C_4$alkyl—SO—, $C_1$-$C_4$alkyl—$SO_2$—, halogen, $CF_3$, —CN, —$NO_2$, —OH, —$COOR_{14}$, $CON(R_{15})_2$, or —$N(R_{15})_2$, or the radical of the formula

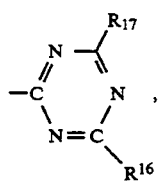

in which $R_{16}$ and $R_{17}$, independently of one another, are $C_1$-$C_6$alkyl, phenyl, $C_1$-$C_6$alkylphenyl or ($C_1$-$C_6$alkyl)$_2$-phenyl, or $R_3$ and $R_4$ or $R_4$ and $R_5$, in each case together, are —CH=CH—CH=CH—, $R_6$ to $R_{12}$, independently of one another, are H, $C_1$-$C_{12}$alkyl, $C_1$-$C_{12}$alkoxy, $C_1$-$C_{12}$alkylthio, $C_1$-$C_{12}$alkyl—SO—, $C_1$-$C_{12}$alkyl—$SO_2$—, benzyl or $C_1$-$C_4$alk-1-yl which is 1-substituted by a total of one or two —CN and/or —$COOR_{14}$, $C_6$-$C_{10}$aryl, $C_7$-$C_{14}$aralkyl, $C_6$-$C_{10}$aryl—CO, $C_6$-$C_{10}$arylthio, $C_6$-$C_{10}$aryl—SO—, $C_6$-$C_{10}$aryl—$SO_2$, $C_7$-$C_{14}$aralkyloxy, $C_7$-$C_{14}$aralkylthio, $C_7$-$C_{14}$aralkyl—SO—, $C_7$-$C_{14}$aralkyl—$SO_2$—, $C_1$-$C_8$acyl—O—, —$COOR_{14}$, —$CON(R_{15})_2$, $C_1$-$C_8$acyl—$NR_{15}$—, $(R_{15})_2$N—, halogen, —$CF_3$ or —CN, or each two adjacent radicals of $R_6$ to $R_{12}$ are the groups —CO—O—CO— or —CO—$NR_{13}$—CO—, the aryl radicals and radicals containing aryl groups being unsubstituted or substituted by halogen, —CN, —$CF_3$, $C_1$-$C_6$alkylthio, $C_1$-$C_6$alkoxy, $C_1$-$C_6$alkyl, —$COOR_{14}$, —CO—$N(R_{15})_2$ or $C_1$-$C_{12}$acyl—O— $R_{13}$ is H, $C_1$-$C_{12}$alkyl or $C_1$-$C_{12}$acyl, phenyl or benzyl, which are unsubstituted or substituted by $C_1$-$C_6$alkyl, $C_1$-$C_6$alkoxy, $C_1$-$C_6$alkylthio, halogen or —$COOR_{14}$, the two $R_{15}$ together are $C_4$-$C_8$alkylene, 3-oxa-1,5-pnetylene, 3-thia-1,5-pentylene, 1,3-butadiene-1,4diyl or 2-aza-1,3-butadiene-1,4-diyl, or the $R_{15}$ radicals, independently of one another, are H, $C_1$-$C_{12}$alkyl, or phenyl or benzyl which is unsubstituted or substituted by $C_1$-$C_6$alkyl, $C_1$-$C_6$alkoxy, $C_1$-$C_6$alkylthio, halogen or —$COOR_{14}$, and $R_{14}$ is H or the radical of an aromatic or aliphatic alcohol minus the OH group, with the exception of 1-phenoxy-4-methylxanthen-9-one.

Alkyl, alkoxy or alkylthio $R_1$ to $R_5$ may be linear or branched and preferably contain from 1 to 6, in particular from 1 to 4, carbon atoms. Examples are methyl, ethyl and the isomers of propyl, butyl, pentyl, hexyl, heptyl, octyl, nonyl, decyl, undecyl, dodecyl, and the corresponding alkoxy and alkylthio radicals. Preference is given to methyl, ethyl, n- and i-propyl, n-, i- and t-tubyl, methoxy, ethoxy, n- and i-propoxy, n-, i- and t-butoxy, methylthio and ethylthio. $C_1$-$C_4$Alkyl—SO— or $C_1$-$C_4$alkyl—$SO_2$— $R_1$ to $R_5$ may be, for example, methyl-, ethyl-, n-propyl- or n-butylsulfinyl or -sulfonyl.

Halogen $R_1$ to $R_5$ may be, for example, —F, —Cl, —Vr or —I.

—$COOR_{14}$ $R_1$ to $R_5$ are preferably —COO—$C_1$-$C_{18}$alkyl; —$N(R_{15})_2$ $R_1$ to $R_5$ are preferably —N($C_1$-$C_6$alkyl)$_2$; and —$CON(R_{15})_2$ $R_1$ to $R_5$ are preferably —CO—N($C_1$-$C_6$alkyl)$_2$ or —CO—NH($C_1$-$C_6$alkyl).

$R_{16}$ and $R_{17}$ are preferably methyl, ethyl, phenyl, methylphenyl or dimethylphenyl.

In a preferred embodiment, $R_1$ to $R_5$, independently or one another, are H, $C_1$-$C_6$alkyl, $C_1$-$C_6$alkoxy, halogen, —$CF_3$, —CN, —$NO_2$, —$COOR_{14}$, —OH, —$N(R_{15})_2$ or $R_3$ and $R_4$ or $R_4$ and $R_5$, in each case together are —CH=CH—CH=CH—, where $R_{14}$ is linear or branched $C_1$-$C_{18}$alkyl, and each $R_{15}$ is $C_1$-$C_6$alkyl.

In another preferred embodiment, at least 2, in particular at least 3, of the radicals $R_1$ to $R_5$ are H.

Alkyl, alkoxy, alkylthio, alkyl—SO— or alkyl—$SO_2$— $R_6$ to $R_{12}$ preferably contain from 1 to 6, in particular from 1 to 4, carbon atoms. Examples and further preferences are as given above for $R_1$ to $R_5$.

$R_6$ to $R_{12}$ as $C_1$-$C_4$alk-1-yl or benzyl which is 1-substituted by a total of one or two —CN and/or —$COOR_{14}$ may be, for example, cyanomethyl, dicyanomethyl, α-cyanobenzyl, 1-cyanoeth-1-yl, 1,1-dicyanoeth-1-yl, (methoxycarbonyl)methyl, (ethoxycarbonyl)methyl, di(methoxycarbonyl)methyl, α-(methoxycarbonyl)benzyl, 1,1-di(methoxycarbonyl)-eth-1-yl or cyano-(methoxycarbonyl)-methyl.

Aryl $R_6$ to $R_{12}$ are preferably naphthyl and in particular phenyl. $R_6$ to $R_{12}$ as radicals conaining aryl groups preferably contain naphthyl and in particular phenyl groups.

Aralkyl $R_6$ to $R_{12}$ are preferably phenyl($C_1$-$C_4$alkyl), in particular benzyl or 1-phenyleth-1-yl or -2-yl.

Aryl-CO— $R_6$ to $R_{12}$ are preferably naphthyl—CO— and in particularphenyl—CO—.

Aryloxy $R_6$ to $R_{12}$ are preferably naphthyloxy and in particular phenoxy.

Arylthio $R_6$ to $R_{12}$ are in particular naphthylthio or phenylthio.

Aryl—SO— or aryl—SO$_2$ $R_6$ to $R_{12}$ are preferably phenyl—SO— or phenyl—SO$_2$—.

Aralkoxy $R_6$ to $R_{12}$ are preferably phenyl($C_1$–$C_4$alkyl—O—, in particular benzyloxy.

Aralkylthio $R_6$ to $R_{12}$ are preferably phenyl($C_1$–$C_4$alkyl—S—, in particular benzylthio.

Aralkyl—SO— $R_6$ to $R_{12}$ are preferably phenyl(-$C_1$–$C_4$alkyl—SO—, in particular benzyl—SO—.

Aralkyl—SO$_2$— $R_6$ to $R_{12}$ are preferably phenyl ($C_1$–$C_4$alkyl—SO$_2$—, in particular benzyl—SO$_2$—.

$C_1$–$C_{18}$Acyl—O— $R_6$ to $R_{12}$ preferably conform to the formula $R_{19}$—CO—O, in which $R_{19}$ is H or $C_1$–$C_{17}$alkyl, $C_2$–$C_{17}$alkenyl, $C_3$–$C_8$cycloalkyl, $C_6$–$C_{10}$aryl or $C_7$–$C_{14}$aralkyl, each of which is unsubstituted or substituted by halogen, preferably —F or —Cl, —OH, $C_1C_6$ alkoxy or $C_1$–$C_6$alkylthio. $R_{19}$ is preferably $C_1$–$C_{12}$alkyl, $C_2$–$C_{12}$alkenyl, cyclopentyl, cyclohexyl, phenyl or benzyl.

If $R_6$ to $R_{12}$ are the group —COOR$_{14}$, $r_{14}$ is in particular $C_1$–$C_{18}$alkyl.

If $R_6$ to $R_{12}$ are the group —CON(R$_{15}$)$_2$ or the group —CONHR$_{15}$, $R_{15}$ are in particular $C_1$–$C_6$alkyl.

If $R_6$ to $R_{12}$ are the group $C_1$–$C_{18}$acyl—NR$_{15}$—, the group preferably conforms to the formula $R_{19}$—CO—NR$_{15}$—, in which $R_{19}$ is as defined for the group $R_{19}$—CO—O—, including the preferences, and $R_{15}$ is preferably H or $C_1$–$C_6$alkyl.

If $R_6$ to $R_{12}$ are the group —N(R$_{15}$)$_2$, each $R_{15}$ is preferably $C_1$–$C_6$alkyl, cyclohexyl, phenyl, benzyl, tetramethylene, pentamethylene, 3-oxa-1,5-pentylene or —CH=CH—CH=CH—.

Halogen $R_6$ to $R_{12}$ are preferably —F, —Cl or —Br.

If $R_6$ to $R_{12}$ are aryl groups or radicals containing aryl groups, these may be unsubstituted, monosubstituted or polysubstituted, preferably monosubstituted or disubstituted, by halogne, preferably —F, —Cl or —Br, —CN, —OH, —CF$_3$, $C_1$–$C_6$alkylthio (for example methylthio or ethylthio), $C_1$–$C_6$alkoxy (for example methoxy, ethoxy, n- or i-propoxy, n-, i- or t-butoxy), $C_1$–$C_6$alkyl (for example methyl, ethyl, n- or i-propyl, n-, i- or t-butyl), —COOR$_{14}$, in which $R_{14}$ is preferably H or $C_1$–$C_{12}$alkl, —CON(R$_{15}$)$_2$, in which $R_{15}$ is preferably H or $C_1$–$C_6$alkyl, or $C_1$–$C_{12}$acyl—O—, preferably $C_1$–$C_{11}$alkyl—CO—O—.

Alkyl $R_{13}$ preferably contains from 1 to 6, in particuar from 1 to 4, carbon atoms and is, for example, methyl or ethyl. Acyl $R_{13}$ is preferably $R_{19}$—CO—, in which $R_{19}$ is as defined above and is in particular $C_1$–$C_8$alkyl, cyclohexyl, phenyl or benzyl.

An alcohol radical $R_{14}$ preferably contains from 1 to 30, in particular from 1 to 20, especially from 1 to 10, carbon atoms. An aromatic alcohol radical $R_{14}$ may be $C_6$–$C_{10}$aryl, in particular phenyl or phenyl($C_1$–$C_4$alkyl), in particular benzyl or 1-phenyleth-2-yl, which may be substituted by 1 or 2 $C_1$–$C_{18}$alkyl, in particular $C_1$–$C_{12}$alkyl groups.

An aliphatic radical $R_{14}$ may be an open-chain or cyclic radical, e.g. $C_1$–$C_{20}$alkyl, in particular $C_1$–$C_{18}$alkyl, especially $C_1$–$C_{12}$alkyl; $C_3$–$C_8$cycloalkyl or $C_3$–$C_8$-cycloalkylmethyl, in particular cyclopentyl, cyclohexyl or cyclohexylmethyl.

$R_{14}$ may alternatively be a polyoxaalkylene radical of the formula —$C_nH_{2n}$—$O_mR_{18}$ in which n is an integer from 2 to 6, in particular from 2 to 4, especially 2 or 3, and m is a number from 1 to 20, in particular 1 to 12, especially 1 to 6, and $R_{18}$ is H, $C_1$–$C_{18}$alkyl, in particular $C_1$–$C_{12}$alkyl, especially $C_1$–$C_6$alkyl, $C_3$–$C_8$cycloalkyl, in particular $C_5$- or $C_6$cycloalkyl or -cycloalkylmethyl; or phenyl or benzyl, which may be substituted by 1 or 2 alkyl groups having from 1 to 12, in particular from 1 to 6, carbon atoms.

Alkyl $R_{15}$ preferably contains from 1 to 5, in particular from 1 to 4, carbon atoms and is in particular methyl or ethyl. Substituted phenyl or benzyl $R_{15}$ preferably contains 1 or 2 substituents. Halogen and —COOR$_{14}$ as substituents are preferably —F, —Cl, —Br, —COOH and —COO($C_1$–$C_{12}$alkyl). The two $R_{15}$ radicals together, as alkylene, are preferably tetramehtylene or pentamethylene.

In a preferred embodiment, at least 2, in particular at least 3 and especially at least 4, of the radicals $R_6$ to $R_{12}$ are H.

A preferred subgroup of compounds of the formula I comprises those in which $R_6$ to $R_{12}$, independently of one another, are H, $C_1$–$C_6$alkyl, $C_1$–$C_6$alkoxy, $C_1$–$C_6$alkylthio, $C_1$–$C_6$alkyl—SO—, $C_1$–$C_6$alkyl—SO$_2$, $C_1$- or $C_2$alkyl which is 1-substituted by a total of one or 2 —CN and/or COOR$_{14}$, phenyl, pneyly-$C_1$–$C_4$alkyl, pnehyl—CO—, phenyloxy, phenylthio, phenyl—SO—, phenyl—SO$_2$—, benzyloxy, benzylthio, benzyl—SO—, benzyl—SO—, $C_1$–$C_8$acyl—NR$_{15}$—, —COOR$_{14}$, —CON(R$_{15}$)$_2$, (R$_{15}$)$_2$N—, —F, —Cl, —Br, —CF$_3$ or —CN or each two adjacent $R_6$ to $R_{12}$ radicals together are —CO—O—CO— or —CO—NR$_{13}$—CO—, $R_{13}$ is $C_1$–$C_6$alkyl, or phenyl or benzyl which are unsubstituted or substituted by $C_1$–$C_4$alkyl, $C_1$–$C_4$alkoxy, F, C, Br or —COOR$_{14}$, $R_{14}$ is H, linear or branched $C_1$–$C_{18}$alkyl, phenyl, benzyl or —$C_nH_{2n}$—$O_mR_{18}$, where n is an integer from 2 to 6, and m is a number from 1 to 20, and $R_{18}$ is H, $C_1$–$C_{18}$alkyl, cyclohexyl, phenyl or benzyl, and $R_{15}$ is $C_1$–$C_6$alkyl, or phenyl or benzyl which is unsubstituted or substituted by $C_1$–$C_4$alkyl, $C_1$–$C_4$alkoxy, —F, —Cl, —Br or —COOR$_{14}$, or the two $R_{15}$ radicals together are 1,4-butylene, 1,5-pentylene, 3-oxa-1,5-pentylene or 1,3-butadiene-1,4-diyl.

Preferred groups of compounds are also those in which, in the formula I, $R_6$ is H, —Cl, —Br or methyl, or in which, in the formula I, $R_9$ is H or —Cl, or in which, in the formula I, $R_{11}$ is H or —Cl, or in which, in the formula I $R_{10}$ and/or $R_{12}$ is —Cl, —Br, unsubstituted or substituted phenoxy or —COO—($C_1$–$C_{12}$alkyl), or in which, in the formula I, $R_7$ and/or $R_8$ is H, —F, —Cl, —CF$_3$, —Br, $C_1$–$C_4$alkyl, $C_1$–$C_4$alkoxy, phenyl—CO—, α-cyanobenzyl, $C_1$–$C_8$acyl—NR$_{15}$—, pyrryl, —COO—($C_1$–$C_{12}$alkyl), or phenoxy, phenylthio or phenylsulfonyl, which are unsubstituted or substituted by —F, —Cl, $C_1$–$C_4$alkoxy, —COOH or —COO—($C_1$–$C_{12}$alkyl), or $R_7$ and $R_8$ together are

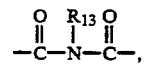

and $R_{13}$ is H or $C_1$–$C_6$alkyl, or in which in the formula I, $R_{13}$ is $C_1$–$C_4$alkyl or $C_1$–$C_8$acyl, or phenyl or benzyl which are unsubstituted or substituted by F or —COOR$_{14}$, and $R_{14}$ is H or $C_1$–$C_{12}$alkyl, or in which, in the formula I, $R_{14}$ is H, $C_1$–$C_{18}$alkyl, —$C_nH_{2n}$—$O_mH$, phenyl, $C_1$–$C_6$alkylphenyl, benzyl, $C_1$–$C_6$alkylbenzyl or cyclohexyl, n is an integer from 1 to 6, and m is a number from 1 to 20, or in which, in the formula I, $R_{15}$ is H, $C_1$–$C_6$alkyl, phenyl, benzyl, or the two $R_{15}$ radicals together are tetramethylene, pentamethylene, 3-oxa-1,5-pentylene or 1,3-butadiene-1,4diyl.

Particularly preferred compounds of the formula I are those in which $R_1$ to $R_5$ are H or $R_1$, $R_2$, $R_4$ and $R_5$ are H and $R_3$ is —$CO_2C_2H_5$, $R_6$ and $R_8$ are Cl, and $R_7$ and $R_9$–$R_{12}$ are H, and X is $NCH_3$ or $N$-$n$-$C_3H_7$.

The compounds according to the invention can be obtained in a manner known per se by nucleophilic substitution of 1-nitro- or 1-haloxanthones, -thioxanthones, -thioxanthone sulfoxides, -thioxanthone sulfodioxides or -acridones by phenol salts. The invention furthermore relates to a process for the preparation of compounds of the formula I which comprises reacting a compound of the formula II

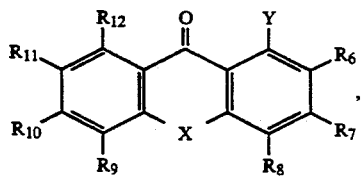

in which X and $R_6$ to $R_{12}$ are as defined in claim 1, and Y is —$NO_2$ or halogen, with a compound of the formula III

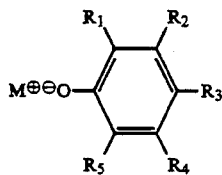

in which $R_1$ to $R_5$ are as defined in claim 1, and $M\oplus$ is an alkali metal cation, or a quaternary ammonium or phonphonium cation, at elevated temperature in the presence of a dipolar aprotic or protic solvent.

The process according to the invention is preferably carried out at temperatures of from 50 to 200° C., in particular from 50 to 150° C. The salts of the formula III can be employed as such or produced in situ in the reaction mixture by reacting an appropriate phenol with an alkali metal, ammonium or phosphonium base. The salts of the formula III can be employed in equimolar amounts or in excess, e.g. an excess of up to 40 mol-%.

Examples of suitable solvents are N-substituted carboxamides and lactams (for example dimethylformamide of N-methylpyrrolidone), sulfoxides and sulfones (for example dimethyl sulfoxide or tatramethylene sulfone) or ethers (for example di-n-propyl ether, di-n-butyl ether, tetrahydrofuran or dioxane).

The compounds of the formula I are isolated and purified by conventional method, for example by crystallization and recrystallization, or by chromatography.

The compounds of the formula III are known or can be obtained in a known manner by reacting appropriate phenols with alkali metal, ammonium or phosphonium bases. Particularly suitable alkali metal cations are Li$\alpha$, Na$\oplus$ and K$\oplus$; and examples of particularly suitable quaternary onium cations are ($C_1$–$C_6$alkyl)$_4$N$\oplus$, ($C_1$–$C_6$alkyl)P$\oplus$ or tetraphenylphosphonium.

Compounds of the formula I containing functional groups, for example —COOH or —$NH_2$, can be derivatized in a known manner to give esters or amides.

Some of the compounds of the formula II in which Y, as halogen, is preferably —F, —Cl or —Br are known or can be prepared by processes known per se by intramolecular Friedel-Crafts acylation (thioxanthones, see, for example U.S. Pat. No. 4,385,182 or F. Mayer, Chem. Ber. 43, pp. 584 ff (1910); xanthones, see, for example, F. Ullmann et al., Chem. Ber. 38 pp. 2120 ff (1905); acridones, see for example, C. W. Renocastle et al., Synthesis 1985, pp. 21 ff). Thioxanthone sulfoxides and sulfodioxides can also be obtained by oxidation of the thioxanthones.

Compounds of the formula I are heat resistant, colourless to slightly yellow and predominantly crystalline and are soluble in organic solvent. They are highly effective photoinitiators and photosensitizers for photopolymerizable or photodimerizable systems which contain ethylenically unsaturated double bonds.

When the compounds are irradiated, alone or in a substrate, with light having a wavelength of from about 300 to 450 nm, a pronounced colour change to blue/violet is surprisingly found. This colour change is irreversible.

The compounds of the formula I can therefore be used as photoinitiators and in particular as photosensitizers in photopolymerizable systems, with a simultaneous action as colour indicators. It is thus possible to mark exposed products (for example protective coatings, printing plates, offset printing circuits, solder stop masks) and to differentiate them from unexposed products, and furthermore to separate out products which have been exposed incorrectly, during product monitoring or after development.

The substantial advantage when used as colour indicators is the increase in the sensitizer action. Additives usually employed as colour-change systems cause a reduction in photosensitivity.

The compounds of the formula I can also be used as such, in solution or incorporated into polymers as colour photoindicators or as photoswitching elements.

The invention furthermore relates to a radiation-sensitive composition containing
a) a radiation-sensitive organic material, and
b) at least one compound of the formula I, including 1-phenoxy-4-methylxanthen-9-one.

The compounds of the formula I can be present in an amount of from 0.001 to 20% by weight, in particular from 0.001 to 10% by weight, especially from 0.01 to 5% by weight, based on component a).

Radiation-sensitive and thus also photostructurable materials are known. They may be positive or negative systems. Such materials are described, for example, by G. E. Green et al., in J. Macro. Sci. Revs. Macr. Chem., C21)2), 187–273 ( (1981–82) and by G. A. Delzenne in Adv. Photochem., 11, pp. 1–103 (1979).

The radiation-sensitive organic material is preferably
a1) a nonvolatile monomeric, oligomeric or polymeric substance containing photopolymerizable or photodimerizable, ethylenically unsaturaged groups, a2) a cationically curable system of a3) photocrisslinkable polyimides.

Examples of photopolymerizable substances are acrylates and in particular methacrylates of polyols, e.g. ethylene glycol, propanediol, butanediol, hexanediol, di(hydroxymethyl)cyclohexane, 2,2-bis(4-hydroxyethoxyphenyl)propane, polyoxyalkylenediols, for example di-, tri- or tetraethylene glycol, di- or tri-1,2-propylene glycol, trimethylolmethane, -ethane or -propane and pentaerythritol, which can be used alone, in mixtures and blended with binders. Products of the addition of acrylic acid and in particular methacrylic acid onto bisglycidyloxy compounds, for example 2,2-bis(4- glycidyloxyphenyl)propane, are also suitable. Methylenebisacrylamide is furthermore suitable.

Examples of photodimerizable substances are homopolymers and copolymers which contain cinnamic acid groups or substituted maleinimidyl compounds in side groups or chalcone groups in the polymer chain.

Preferred compositions of this type are those in which component a1) is a homopolymer or copolymer of acrylates, methacrylates or maleates whose ester groups contain a radical of the formula

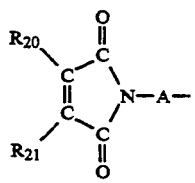

in which A is unsubstituted or hydroxyl-substituted, linear or branched $C_2$-$C_{12}$alkylene, cyclohexylene or phenylene, and $R_{20}$ and $R_{21}$, independently of one another, are Cl, Br, phenyl or $C_1$-$C_4$alkyl, or $R_{20}$ and $R_{21}$ together are trimethylene, tetramethylene or

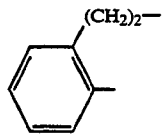

Polymers of this type are described, for example, in U.S. Pat. No. 4,193,927.

The photopolymerizable or photodimerizable substances may contain further additives which are customary for processing or application and in addition other photoinitiators or photosensitizers.

The cationically curable systems are preferably epoxide compounds containing at least two epoxide groups in the molecule and mixed with a photoinitiator. Examples of suitable photoinitiators are metallocenes, metallocene carbonyls and onium salts, which are described, for example, in the abovementioned publications. The curable systems may contain additives which are customary for processing and application.

Photosensitive polyimides are described, for example, in DE-A-1, 962 588, EP-A-0 132 221, EP-A-0 134 752, EP-A-0 162 017, EP-A-0 181 837 and EP-A-0 182 745.

The composition according to the invention is applied as a coating to substrates by known methods, and either a protective coating is produced by irradiation over the entire area or a relief image is produced by irradiation under a photomask with subsequent development.

The invention furthermore relates to a composition containing a) a colourless, organic solvent, a polymer or an organic glass or a composite glass, and b) a compound of the formula I, including 1-phenoxy-4-methylxanthen-9-one. Component b) is preferably present in an amount of from 0.001 to 20% by weight, in particular from 0.001 to 10% by weight, especially from 0.01 to 5% by weight based on component a). Organic solutions can be used to coat other substances, e.g. inorganic glasses, which can then be used as photoswitchable substrates. The compounds of the formula I can also be sublimed onto substrates. The coated substartes can be provided with a protective coating of, for example, transparent polymers. Examples of suitable solvents are hydrocarbons, halogenated hydrocarbons, ketones, carboxylic acid esters and lactones, N-alkylated acid amides and lactams, alkanols and ethers.

Examples of suitable polymers are thermosets, thermoplastics and structurally crosslinked polymers. The polymers are preferably transparent. Such polymers and organic glasses are known to those skilled in the art. The compounds according to the invention are incorporated by conventional methods, e.g. by dissolution and removal of the solvent, calendering or extrusion. The compounds according to the invention can also be incorporated into the substrates before, during or after preparation.

The invention furthermore relates to a process for the production of coloured materials under the action of light, which comprises incorporating a compound of the formula I, includign 1-phenoxy-4-methylxanthen-9-one, into the material and then irradiating the material with light.

The invention furthermore relates to the use of compounds of the formula I, including 1-phenoxy-4-methylxanthen-9-one, as photosensitizers and colour indicators or photoswitching elements under the action of light.

The examples below illustrate the invention in greater detail.

A) PREPARATION EXAMPLES

Examples A1–A76

16 mmol of 1-haloxanthone, -thioxanthone or -acridone, 24 mmol of phenol, 40 mmol of potassium carbonate and 45 ml of solvent are warmed with stirring. The reactio mixture is poured into 200 ml of ice, and the precipitate is filtered off and dissolved in toluene/tetrahydrofuran (1:1). The solution is washed successively with 5% strength NaOH, water and saturated aqueous sodium chloride solution, and dried using sodium sulfate. The solvent is removed by distillation, and the residue is recrystallized from toluene/isopropanol (1:1).

Further details are given tin Tables 1a and 1b. The data relate to the formula

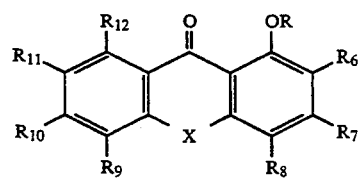

TABLE 1a

| No. A | X | R | R6 | R7 | R8 | R9 | R10 | R11 | R12 | Melting point (°C.) |
|---|---|---|---|---|---|---|---|---|---|---|
| 1 | O | Ph | H | OPh | H | H | H | H | Cl | 168-176 |
| 2 | O | Ph | H | OPh | H | H | H | H | OPh | 181-183 |
| 3 | O | Ph | H | OPh | H | Cl | OPh | Cl | CO2C2H5 | 195-197 |
| 4 | O | Ph | H | Cl | H | Cl | H | H | Cl | 152-154 |
| 5 | N-3,5-F2Ph | Ph | H | Cl | H | H | H | H | CO2C2H5 | 229-231 |
| 6 | NC2H5 | Ph | H | F | H | H | H | H | H | 189-191 |
| 7 | NCH2Ph | Ph | H | Cl | H | H | H | H | H | 223-225 |
| 8 | NCH3 | Ph | H | F | H | H | H | H | H | 100-105 |
| 9 | NCH3 | Ph | H | OPh | H | H | H | H | CF3 | 142-145 |
| 10 | N-2-COOH—Ph | Ph | H | H | H | H | H | H | H | <260 |
| 11 | NC2H5 | 3-Br—Ph | H | Cl | H | H | H | H | H | 183-187 |
| 12 | NC2H5 | 4-Cl—Ph | H | Cl | H | H | H | H | H | 147-148 |
| 13 | NC2H5 | Ph | H | PhO | H | H | H | H | H | 164-65 |
| 14 | NC2H5 | 3-Br—Ph | H | 3-BrPhO | H | H | H | H | H | 126-129 |
| 15 | NCH3 | Ph | H | H | Cl | H | H | H | H | 129-130 |
| 16 | NC2H5 | 3,5-(CH3O)2Ph | H | 3,5-(CH3O)2PhO | H | H | H | H | H | 152-154 |
| 17 | NC2H5 | 3,5-(CH3O)2Ph | H | Cl | H | H | H | H | H | 180-183 |
| 18 | NC2H5 | 4-Cl—Ph | H | 4-ClPhO | H | H | H | H | H | 148-149 |
| 19 | NC2H5 | 4-(oct-2-yl-O2C)Ph | H | Cl | H | H | H | H | H | Oil |
| 20 | NC2H5 | 4-(oct-2-yl-O2C)Ph | H | Cl | H | H | H | H | H | Oil |
| 21 | NC2H5 | 4-(C2H5O2C)Ph | H | Cl | H | H | H | H | H | 138-140 |
| 22 | Ni-propyl | Ph | H | Cl | H | H | H | H | H | 143-145 |
| 23 | NCHCH3 CO2C2H5 | Ph | H | Cl | H | H | H | H | H | 144-147 |
| 24 | NCHCH3 CO2C2H5 | Ph | H | OPh | H | H | H | H | H | 60-70 |
| 25 | NCH2—CH-nC4H9 C2H5 | Ph | H | Cl | H | H | H | H | H | 102-104 |
| 26 | NCH2—CH-nC4H9 C2H5 | Ph | H | OPh | H | H | H | H | H | 102-105 |
| 27 | NC2H5 | Ph | H | Cl | H | H | H | H | H | 128-130 |
| 28 | NCH3 | Ph | Cl | H | Cl | H | H | H | H | 173-174 |
| 29 | NC3H7 | Ph | Cl | H | Cl | H | H | H | H | 116-118 |
| 30 | S | Ph | Cl | Cl | Cl | H | H | H | H | 190-192 |
| 31 | S | Ph | Br | PhO | F | H | H | H | H | 203-204 |
| 32 | S | Ph | H | H | CH3O | H | H | H | H | 199-202 |
| 33 | S | Ph | Cl | H | Cl | H | H | H | H | 191-193 |
| 34 | S | Ph | Cl | H | Cl | H | H | H | H | 183-185 |
| 35 | S | 4-NO2—Ph | Cl | H | Cl | H | H | H | H | 228-230 |
| 36 | S | 4-F—Ph | Cl | H | Cl | H | H | H | H | 149-150 |
| 37 | S | 4-Br—Ph | Cl | H | Cl | H | H | H | H | 217-219 |
| 38 | S | 4-Cl—Ph | Cl | H | Cl | H | H | H | H | 192-195 |

TABLE 1a-continued

| No. A | X | R | R6 | R7 | R8 | R9 | R10 | R11 | R12 | Melting point (°C.) |
|---|---|---|---|---|---|---|---|---|---|---|
| 40 | S | 4-I—Ph | Cl | H | Cl | H | H | H | H | 236-238 |
| 41 | S | 4-CH3—Ph | Cl | H | Cl | H | H | H | H | 175-177 |
| 42 | S | 4-CH3O—Ph | Cl | H | Cl | H | H | H | H | 153-155 |
| 43 | S | (C2H5)2N—Ph | Cl | H | Cl | H | H | H | H | 134-135 |
| 44 | S | 3-Cl—Ph | Cl | H | Cl | H | H | H | H | 150-152 |
| 45 | S | 3-CH3O—Ph | Cl | H | Cl | H | H | H | H | 169-171 |
| 46 | S | 3,5-(CH3O)2-Ph | Cl | H | Cl | H | H | H | H | 192-194 |
| 47 | S | 2,4-Cl2—Ph | Cl | H | Cl | H | H | H | H | 235-237 |
| 48 | S | 3-Br—Pr | Cl | H | Cl | H | H | H | H | 172-174 |
| 49 | S | 3,4-Cl2—Ph | Cl | H | Cl | H | H | H | H | 187-188 |
| 50 | S | Ph | Cl | H | Cl | H | H | H | H | 178-183 |
| 51 | S | 4-CN—Ph | Cl | H | Cl | H | H | H | H | 248-251 |
| 52 | S | 4-(C2H5O2C)-Ph | Cl | H | Cl | H | H | H | H | 172-174 |
| 53 | S | 4-t-ocytl-Ph | Cl | H | Cl | H | H | H | H | 137-139 |
| 54 | S | 4-(n-C12H25O2C)-Ph | Cl | H | Cl | H | H | H | H | 109-112 |
| 55 | S | Ph | Cl | H | Cl | H | H | H | H | 170-173 |
| 56 | S | Ph | CH3 | H | CH3 | H | C2H5O2C | CO2C2H5 | C2H5O2C | 153-155 |
| 57 | S | 4-(n-C12H25O2C)-Ph | Cl | H | Cl | H | H | H | H | 129-133 |
| 58 | S | 3-(C2H5O2C)-Ph | Cl | H | Cl | H | C2H5O2C | H | H | 163-165 |
| 59 | S | 3-CF3—Ph | Cl | H | Cl | H | H | H | H | 167-169 |
| 60 | S | Ph | Cl | H | Cl | H | H | H | C2H5O2C | 168-170 |
| 61 | S | Ph | Cl | H | Cl | H | H | H | C2H5CHO2C—n-C5H11 | 127-129 |
| 62 | S | 4-(n-C12H22O2C)-Ph | Cl | H | Cl | H | H | H | C2H5CHO2C—n-C5H11 | Oil |
| 63 | S | 1-naphthyl | Cl | H | Cl | H | H | H | H | 247-249 |
| 64 | S | 2-naphthyl | Cl | H | Cl | H | H | H | H | 197-200 |
| 65 | S | 3-OH-4-R'—Ph | Cl | Cl | Cl | H | H | H | H | 235-238 |
| 66 | S | Ph | H | PhO | H | H | H | H | H | 114-116 |
| 67 | S | Ph | H | Cl | H | H | H | H | H | 151-153 |
| 68 | S | 2,4-Cl2—Ph | H | 3,5-Cl2—Ph | H | H | H | H | H | 205-208 |
| 69 | S | 3,5-Cl2—Ph | H | H | H | H | H | H | H | 195-197 |
| 70 | S | 3,5-Cl2—Ph | Cl | Cl | Cl | H | H | H | H | 202-204 |
| 71 | S | 3,5-Cl2—Ph | H | Cl | H | H | H | H | H | 214-218 |
| 72 | S | Ph | Cl | Cl | Cl | H | H | H | H | 162-165 |
| 73 | S | 3-CH3O—Ph | Cl | Cl | Cl | H | H | H | H | 102-104 |
| 74 | S | 3-CH3O—Ph | Cl | Cl | Cl | H | H | H | H | 172-174 |
| 75 | S | 3-CH3O—Ph | Cl | 3-CH3O—Ph— | Cl | H | H | H | H | — |
| 76 | S | Ph | Br | H | Br | H | H | H | H | 174-176 |

TABLE 1b

| No. A | 1-Halogen | Solvent | Reaction temperature (°C.) | Reaction time (h) | Yield (%) |
|---|---|---|---|---|---|
| 1 | Cl | DMSO | 120 | 19 | 4 |
| 2 | Cl | DMSO | 120 | 19 | 7 |
| 3 | Cl | DMSO | 120 | 18 | 53 |
| 4 | Cl | Bu$_2$O | 120 | 23 | 52 |
| 5 | Cl | Bu$_2$O | 130 | 21 | 44 |
| 6 | F | Dioxane | 100 | 3 | 33 |
| 7 | Cl | Bu$_2$O | 150 | 72 | 84 |
| 8 | F | Dioxane | 100 | 4 | 76 |
| 9 | Cl | DMSO | 120 | 2 | 78 |
| 10 | F | DMSO | 100 | 36 | 45 |
| 11 | Cl | DMSO | 130 | 18 | 58 |
| 12 | Cl | Bu$_2$O | 140 | 24 | 72 |
| 13 | Cl | Bu$_2$O | 140 | 16 | 66 |
| 14 | Cl | DMSO | 140 | 23 | 80 |
| 15 | Cl | DMSO | 140 | 23 | 75 |
| 16 | Cl | DMSO | 130 | 24 | 71 |
| 17 | Cl | DMSO | 140 | 18 | 52 |
| 18 | Cl | Bu$_2$O | 140 | 64 | 24 |
| 19 | Cl | DMSO | 140 | 19 | 72 |
| 20 | Cl | Bu$_2$O | 140 | 40 | 95 |
| 21 | Cl | DMSO | 140 | 61 | 54 |
| 22 | Cl | Bu$_2$O | 140 | 42 | 31 |
| 23 | Cl | DMSO | 140 | 45 | 64 |
| 24 | Cl | Bu$_2$O | 140 | 5 days | 21 |
| 25 | Cl | Bu$_2$O | 140 | 5 days | 15 |
| 26 | Cl | Bu$_2$O | 140 | 68 | 61 |
| 27 | Cl | Bu$_2$O | 140 | 68 | 8 |
| 28 | Cl | Bu$_2$O | 140 | 69 | 53 |
| 29 | Cl | NMP | 100 | 18 | 93 |
| 30 | Cl | DMSO | 110 | 3 | 83 |
| 31 | Cl | Dioxane | 120 | 24 | 44 |
| 32 | Cl | Dioxane | 120 | 24 | 13 |
| 33 | F | Bu$_2$O | 130 | 17 | 75 |
| 34 | F | DMSO | 130 | 9 | 36 |
| 35 | Cl | DMSO | 90 | 23 | 58 |
| 36 | Cl | DMSO | 120 | 23 | 17 |
| 37 | Cl | DMSO | 90 | 23 | 58 |
| 38 | Cl | DMSO | 80 | 28 | 55 |
| 39 | Cl | DMSO | 80 | 28 | 51 |
| 40 | Cl | DMSO | 80 | 17 | 48 |
| 41 | Cl | DMSO | 80 | 17 | 58 |
| 42 | Cl | DMSO | 80 | 19 | 65 |
| 43 | Cl | DMSO | 100 | 20 | 34 |
| 44 | Cl | DMSO | 80 | 21 | 61 |
| 45 | Cl | DMSO | 100 | 6 | 55 |
| 46 | Cl | DMSO | 100 | 18 | 64 |
| 47 | Cl | DMSO | 120 | 24 | 47 |
| 48 | Cl | DMSO | 80 | 18 | 60 |
| 49 | Cl | DMSO | 100 | 18 | 56 |
| 50 | Cl | DMSO | 80 | 3 | 70 |
| 51 | Cl | DMSO | 100 | 19 | 58 |
| 52 | Cl | DMSO | 100 | 15 | 61 |
| 53 | Cl | DMSO | 80 | 16 | 53 |
| 54 | Cl | DMSO | 100 | 18 | 49 |
| 55 | Cl | DMSO | 80 | 18 | 55 |
| 56 | Br | DMSO | 140 | 32 | 3 |
| 57 | Cl | DMSO | 90 | 22 | 57 |
| 58 | Cl | DMSO | 80 | 22 | 56 |
| 59 | Cl | DMSO | 90 | 6 | 61 |
| 60 | Cl | DMSO | 80 | 16 | 67 |
| 61 | Cl | DMSO | 80 | 6 | 65 |
| 62 | Cl | DMSO | 100 | 6 | 88 |
| 63 | Cl | DMSO | 100 | 22 | 52 |
| 64 | Cl | DMSO | 100 | 22 | 58 |
| 65 | Cl | DMSO | 100 | 18 | 73 |
| 66 | Cl | Dioxane | 100 | 47 | 63 |
| 67 | Cl | DMSO | 120 | 20 | 97 |
| 68 | Cl | Dioxane | 100 | 72 | 27 |
| 69 | Cl | Dioxane | 100 | 72 | 80 |
| 70 | Cl | DMSO | 120 | 18 | 70 |
| 71 | Cl | DMSO | 100 | 3 | 46 |
| 72 | Cl | Bu$_2$O | 130 | 96 | 42 |
| 73 | Cl | Dioxane | 100 | 72 | 52 |
| 74 | Cl | Bu$_2$O | 140 | 7 | 80 |
| 75 | Cl | — | — | — | 4[1] |
| 76 | Br | Bu$_2$O | 140 | 20 | 69 |

Abbreviations:
DMSO: Dimethyl sulfoxide
Bu$_2$O: Di-(n-butyl) ether
NMP: N-methylpyrrolidone
Ph: Phenyl

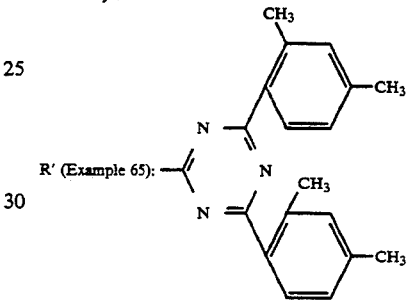

R' (Example 65):

[1] Byproduct from Example A74

Examples A77–A82

340 mg (1 mmol) 3-chloro-1-phenoxythioxanthone, 3 ml (75 mmol) of methanol and 420 mg (3 mmol) of potassium carbonate are heated at 110° C. for 24 hours in 5 ml of dimethyl sulfoxide. The reaction mixture is poured into water and neutralized using dilute hydrochloric acid, and the product is extracted with toluene/tetrahydrofuran. The organic phase is washed with saturated aqueous sodium bicarbonate solution, dried using sodium sulfate and evaporated. The residue is purified by chromatography (silica gel, hexane/ethyl acetate 10:1) and subsequently recrystallized from toluene. Yield: 113 mg (34%), melting point 154–156° C.

The following compounds (Table 2) are prepared analogously using sodium phenylsulfinate, thiophenol, sodium methylmercaptide or thiosalicylic acid:

| Example No. A | X | R | R$_6$ | R$_7$ | R$_8$ | R$_9$ | R$_{10}$ | R$_{11}$ | R$_{12}$ | Yield (%) | Melting point (°C.) |
|---|---|---|---|---|---|---|---|---|---|---|---|
| 78 | S | Ph | H | —SO$_2$Ph | H | H | H | H | H | 80 | 201–204 |
| 79 | S | Ph | H | —SPh | H | H | H | H | H | 78 | 161–163.5 |
| 80 | S | Ph | H | —SCH$_3$ | H | H | H | H | H | 5 | 173–176 |
| 81 | S | Ph | H | 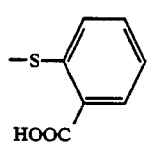 | Cl | H | H | H | H | 46 | 247–250 |

-continued

| Example No. A | X | R | R6 | R7 | R8 | R9 | R10 | R11 | R12 | Yield (%) | Melting point (°C.) |
|---|---|---|---|---|---|---|---|---|---|---|---|
| 82 | S | Ph | H | —S—(C6H4)—COOH | H | H | H | H | H | 50 | 150–152 |

Example A83

N-Methyl-phenoxy-4-pyrrolyacridone 1.3 g (4 mmol) of 4-aminoN-methyl-1-phenoxyacridone and 0.8 g (6 mmol) of 2,5-dimethoxytetrahydrofuran are heated at 130° C. for 30 minutes in 10 ml of glacial acetic acid. The reaction mixture is then poured into 100 ml of water, and the product is extracted with toluene/tetrahydrofuran. The organic phase is washed successively with saturated aqueous socium bicarbonate solution, water and saturated aqueous sodium chloride solution, dried using sodium sulfate and evaporated. Purification by column chromatogrpahy (silica gel, ether/hexane 1:1) and subsequent recrystallization from toluene/isopropanol gives the desired product. Further details are given in Table 3.

Examples A84–A86

The compounds of Examples A84–A86 are prepared analogously to Example A83, with 2,5-dimethoxytetrahydrofuran being replaced in Example A85 by 2,3-dimethylsuccinic anhydride and in Example A86 by dimethylmaleic anhydride. Further details are given in Table 3.

of 4-amino-N-methyl-1-phenoxyacridone in 20 ml of chloroform, and the mixture is stirred at room temperature for 6 hours. The solution is washed with hydrochloric acid (18%), water and saturated aqueous sodium chloride solution, dried using sodium sulphate and evaporated. The residue is washed with diethyl ether and filtered off. Yield: 0.6 g (83%) melting point: 252°–254° C.

Example A88 and A89

The following are obtained in an analogous manner to that in Example A87:

A88: 4-(2Ethylhexanoylamino)-N-methyl-1-phenoxyacridone, melting point 154°–156° C., yield 70%.

A89: 4-(3-Chloro-2,2-dimethylpropionylamino)-N-methyl-1-phenoxyacridone, melting point: 217°–218° C., yield: 80%.

Example A90

2,4-Dichloro-1-phenoxythioxanthone sulfoxide

A colution of 3 g (8 mmol) of 2,4-dichloro-1-phenoxythioxanthone and 0.9 g (8 mmol) of H2O2 (30%) in 100 ml of glacial acetic acid is refluxed for 1 hour. The mixture is subsequently poured into 250 ml of water and

TABLE 3

| Example No. A | X | R | R6 | R7 | R8 | R9 | R10 | R11 | R12 | Yield (%) | Melting point (°C.) |
|---|---|---|---|---|---|---|---|---|---|---|---|
| 83 | NCH3 | Ph | H | H | —N(pyrrolyl) | H | H | H | H | 87 | 177–180 |
| 84 | S | Ph | H | H | —N(pyrrolyl) | H | H | H | H | 64 | 164–166 |
| 85 | NCH3 | Ph | H | H | —N(2,3-dimethylsuccinimido) | H | H | H | H | 85 | 221–223 |
| 86 | NCH3 | Ph | H | H | —N(dimethylmaleimido) | H | H | H | H | 79 | 248–249 |

Example A87

4-Acetlyamino-N-methyl-1-pheonzyacridone 1.3 ml (16 mmol) pyridine and 0.28 ml (4 mmol) of acetyl chloride are added to a solution of 0.7 g (2 mmol)

extracted with 150 ml of toluene. The organic phase is washed with water, aqueous sodium bicarbonate solution (10%) and saturated aqueous sodium chloride solution, dired using sodium sulfate and evaporated. The residue is recyrstallized from toluene/isopropanol. Yield 2.1 g (67%) melting point: 207°-209° C.

Example A91

2,4-Dichloro-1-phenoxythioxanthone sulfodioxide

If the reaction is carried out using 2.7 g of $H_2O_2$ (24 mmol) 30%) and the product is purified by column chromatography (silica gel, $CH_2Cl_2$), 3.26 g (74%) of the sulfone are obtained; melting point: 197°-198° C.

Example A92

1-(3',5'-Dichlorophenoxy)-3-(α-cyclobenzyl)thioxanthone 2 g (4.9 mmol) of 1-(3',5'-dichlorophenoxy)-3-chlorothioxianthone, 0.86 g of benzyl cyanide, 2.03 g of potassium carbonate and 20 ml of DMSO are stirred at 80° C. for 6 hours. The mixture is discharged into 2N HCl/tetrahydrofuran/toluene, and the organic phase is separated off, dried over sodium sulfate and evaportaed. Chromatography on silica gel using methylene chloride gives 0.72 g (30%) of product, melting point 145°-155° C.

Example A93

1-(3',5'-Dichlorophenoxy)-3-benzoylthioxanthone 0.3 g (0.61 mmol) of the compound of Example A92 is stirred at 60° C. with 130 mg (0.92 mmol) of potassium carbonate and 5 ml of DMSO. Air is passed into the mixture for 6 hours at 60° C. The mixture is worked up as in Example A92, and the crude product is recrystallized from methylene chloride/pentane. Yield 0.20 g (69%), melting point 160°-163° C.

Example A94

1Phenoxythioxanthone 3,4-N-butylimide 3.0 g (7.8 mmol) of 1-nitrothioxanthone 3,4-N-butylimide, 0.89 g (9.4 mmol) of phenol, 2.16 g (15.7 mmol) of potassium carbonate and 30 ml of DMSO are stirred at 25° C. for 2 hours. The mixture is discharged into 2N HCl/methylene chloride. The organic phase is separated off, dried over sodium sulfate and evaporated. Recrystallization from methylene chloride/pentane gives 2.88 g (86%) of product of melting point 198°-199° C.

Examples A95 and A96

The following compounds are obtained analogously to Example A94, using the appropriate phenols:

A95: 1-(3,5-Dichlorophenoxy)thioxanthone 3,4-N-butylmide, melting point 207°-213° C., yield 81%.

A96: 1-(2-Methoxy-4-formylphenoxy)thioxanthone 3,4-N-butylimide, melting point 260°-263° C., yield 78%.

Example A97

2,4-Dichloro-1-(3-hydroxyphenyl)-N-methylacridone 8 g (25.6 mmol) of N-methyl-1,2,4-trichloroacridone, 8.46 g (76.8 mmol) of resorcinol, 14.15 g (102.4 mmol) of potassium carbonate and 80 ml of NMP are stirred at 60° C. for 30 hours. The mixture is discharged into water/tetrahydrofuran/toluene. The organic phase is washed with water, dried over sodium sulfate, filtered through silica gel and evaporated. The residue is chromatographed on silica gel using methylene chloride. The fractions containing the product are evaporated, and the residue is recrystallized from o-dichlorobenzene. Yield: 5.45 g (55%), melting point 220°-222° C.

B) USE EXAMPLES

Example B1

1.8 g of the compound from Example A6 are dissolved in 60 mg of methyl methacrylate, and 3.6 mg of azobisisobutyronitrile are added. Using a syringe, with exclusion of air, the solution is transferred into a cell comprising two glass plates with a PVC tube of external diameter 3 mm as spacer. After 18 hours at 70° C. in a circulation oven, the method methacrylate has polymerized completely. The clear plate obtained in this way is cut into strips and employed for exposure experiments. On exposure under a mask using a 5000 W mercury high-pressure lamp at a distance of 80 cm, a dark blue negative image of the mask is obtained.

Examples B2-B5

Colour change systems as light indicators, photosensitizers and photoinitiators

Solutions comprising 100 g of technical grade epoxide-cresol novolak (epoxide value 4.5 eq/kg), 50 g of a tecnical grade bisphenol A diglycidyl ether (epoxide value 0.35 eq/kg), 30 g of Ultramix talc (cyprus), 180 g of cyclohexanone, $5 \times 10^{-3}$ mol of the compounds according to the invention listed in Table 4, and 4 g of ($\eta^6$-cumene)($\eta^5$-cyclopentadienyl)iron(II) trifluoromethanesulfonate are applied to a circuit board using a wire doctor blade. The initially wet film is dried at 80° C. Exposure of the plates produced in this way is carried out using a 5000 watt mercury high-pressure lamp at a distance of 50 cm from teh superimposed mask (Stouffer wedge). The exposure time is 1 minute. The plate is then pre-cured at 110° C. for 10 minutes. The development is carried out in cyclohexanone, the unexposed areas (solder eyes) being dissolved. The plates are then post-cured at 135° C. for 30 minutes. The plates obtained in this way are dipped into a solder bath (270° C.) for 10 seconds, during which no changes are observed.

The colour changes and the final wedge step of the Stouffer wedge (FWS) to be imaged are shown in Table 4.

TABLE 4

| Example No. | Compound from Example | Colour change | FWS |
|---|---|---|---|
| B2 | A69 | Colourless/cyan | 7 |
| B3 | A70 | Colourless/violet | 8 |
| B4 | A7 | Colourless/violet | 10 |
| B5 | A93 | Colourless/green | 10 |

Examples B6-B74

The suitability of these materials is tested in two formulations of photosensitive offset plate coatings:

Formulation I contains only the compounds according to the invention and no additional sensitizer.

It comprises:
1) 2.50 g of a copolymer comprising 86 parts by weight of 6-(dimethylmaleinimidyl)hex-1-yl methacrylate and 14 parts by weight of methacrylic acid (40% by weight in methoxypropanol), $\overline{M}_w$:100000
2) 5.00 ml of the comound according to the invention (1% by weight in dimethylformamide)

3) 0.50 ml of Rhodamine B (dye), 1% by weight in ethylcellulose
4) 2.50 ml of ethyl glycol acetate.

Formulation II contains, in addition to the compounds according to the invention, an additional, commercially available sensitizer.
1) 2.50 g as in formulation I
2) 2.50 ml of the compound according to the invention (2% by weight in dimethylformamide)
3) 2.50 ml of dioctyl 3,4-thioxanthonedicarboxylate, 2% by weight in dimethylformamide
4) 0.50 ml of Rhodamine B, 1% by weight in ethylcellulose
5) 2.50 ml of ethyl glycol acetate The formulations are applied to an offset plate substrate, i.e. aluminium sheet which has been electrolytically roughened and anodized, by spin coating (30 seconds at 500 rpm), and dried at 80° C. for 15 minutes, giving a coating weight of 1.1–1.5 g/m$^2$. The coating is then exposed through a Stouffer wedge (increments of optical density O.D.=0.15) using a 2000 watt metal halide lamp for 100 seconds (distance 75 cm from the vacuum frame). Development is carried out manually at 20° C. by gentle rubbing for 45 seconds with a wad soaked in the following developer solution:
75.0 g of sodium metasilicate pentahydrate
0.4 g of wetting agent (Supronic B 50, ABM Chemicals Ltd.)
925.0 g of demineralized water.

The plates are briefly rinsed with tap water and allowed to dry, and the photosensitivity is then assessed by determining the final wedge step of the numbered Stouffer wedge (FWS) to be imaged. The more wedge steps imaged at a certain exposure energy, the higher the photosensitivity of the coating.

Virtually all the formulations used here give offset printing plates of high photosensitivity and good abrasion resistance, which permits large print runs.

The results are shown in Table 5. The quality of the colour change directly after exposure is given a grade:
1 = image poorly visible
2 = image readily visible
3 = image very readily visible.

The duration in time of the image (image stability) was also assessed by carrying out a qualitative check after 1 hour and after 24 hours for any fading of the image.

TABLE 5

| Example No. | Compound from Example No. | Formulation I | | | Formulation II | | |
|---|---|---|---|---|---|---|---|
| | | FWS | Colour change | Image stability (h) | FWS | Colour change | Image stability (h) |
| B6 | A92 | 10 | 3 | 1 | 10 | 3 | 1 |
| B7 | A9 | 7 | 2 | 24 | 9 | 2 | 24 |
| B8 | A67 | 5 | 1 | 24 | 8 | 1 | 24 |
| B9 | A95 | 10 | 3 | 24 | 10 | 3 | 24 |
| B10 | A68 | 7 | 1 | 24 | 9 | 1 | 24 |
| B11 | A69 | 7 | 1 | 24 | 8 | 1 | 24 |
| B12 | A70 | 6 | 1 | 24 | 8 | 1 | 24 |
| B13 | A71 | 9 | 2 | 24 | 9 | 2 | 24 |
| B14 | A92 | 11 | 2 | 24 | 9 | 2 | 24 |
| B15 | A66 | 7 | 1 | 24 | 10 | 1 | 24 |
| B16 | A78 | 9 | 2 | 24 | 9 | 2 | 24 |
| B17 | A79 | 7 | 2 | 24 | 9 | 2 | 24 |
| B18 | A80 | 3 | 1 | 24 | 7 | 1 | 24 |
| B19 | A73 | 6 | 1 | 24 | 9 | 2 | 24 |
| B20 | A74 | 5 | 2 | 24 | 9 | 2 | 24 |
| B21 | A35 | 8 | 2 | 24 | 10 | 2 | 24 |
| B22 | A36 | 7 | 1 | 24 | 10 | 1 | 24 |
| B23 | A37 | 7 | 2 | 24 | 9 | 2 | 24 |
| B24 | A38 | 7 | 2 | 24 | 9 | 2 | 24 |
| B25 | A39 | 6 | 2 | 24 | 9 | 2 | 24 |
| B26 | A40 | 6 | 2 | 24 | 9 | 2 | 24 |
| B27 | A41 | 6 | 2 | 24 | 8 | 2 | 24 |
| B28 | A42 | 0 | 1 | 24 | 7 | 1 | 24 |
| B29 | A43 | 0 | 1 | 24 | 5 | 1 | 24 |
| B30 | A44 | 7 | 2 | 24 | 9 | 2 | 24 |
| B31 | A45 | 6 | 2 | 24 | 8 | 2 | 24 |
| B32 | A46 | 6 | 2 | 24 | 8 | 2 | 24 |
| B33 | A47 | 7 | 2 | 24 | 8 | 2 | 24 |
| B34 | A48 | 7 | 2 | 24 | 9 | 2 | 24 |
| B35 | A49 | 8 | 2 | 24 | 9 | 2 | 24 |
| B36 | A6 | 8 | 3 | 24 | 9 | 3 | 24 |
| B37 | A34 | 4 | 1 | 1 | 7 | 1 | 1 |
| B38 | A33 | 6 | 2 | 24 | 8 | 2 | 24 |
| B39 | A84 | 6 | 1 | 24 | 8 | 1 | 24 |
| B40 | A34 | 9 | 2 | 24 | 9 | 2 | 24 |
| B41 | A50 | 6 | 2 | 24 | 8 | 2 | 24 |
| B42 | A51 | 8 | 2 | 24 | 10 | 2 | 24 |
| B43 | A52 | 7 | 2 | 24 | 8 | 2 | 24 |
| B44 | A53 | 5 | 2 | 24 | 8 | 2 | 24 |
| B45 | A54 | 6 | 2 | 24 | 7 | 2 | 24 |
| B46 | A58 | 7 | 2 | 24 | 9 | 2 | 24 |
| B47 | A59 | 8 | 2 | 24 | 9 | 2 | 24 |
| B48 | A55 | 6 | 2 | 24 | 7 | 2 | 24 |
| B49 | A57 | 8 | 2 | 24 | 8 | 2 | 24 |
| B50 | A60 | 6 | 2 | 24 | 8 | 2 | 24 |
| B51 | A61 | 6 | 2 | 24 | 9 | 2 | 24 |
| B52 | A62 | 7 | 2 | 24 | 8 | 2 | 24 |
| B53 | A63 | 0 | 2 | 24 | 6 | 2 | 24 |
| B54 | A64 | 4 | 1 | 24 | 7 | 1 | 24 |

TABLE 5-continued

| Example No. | Compound from Example No. | Formulation I | | | Formulation II | | |
|---|---|---|---|---|---|---|---|
| | | FWS | Colour change | Image stability (h) | FWS | Colour change | Image stability (h) |
| B55 | A12 | 9 | 2 | 24 | 9 | 2 | 24 |
| B56 | A13 | 8 | 2 | 24 | 9 | 2 | 24 |
| B57 | A14 | 5 | 2 | 24 | 8 | 2 | 24 |
| B58 | A15 | 6 | 2 | 24 | 8 | 2 | 24 |
| B59 | A16 | 9 | 2 | 24 | 9 | 2 | 24 |
| B60 | A17 | 5 | 2 | 24 | 8 | 2 | 24 |
| B61 | A18 | 8 | 3 | 24 | 9 | 3 | 24 |
| B62 | A19 | 7 | 2 | 24 | 9 | 2 | 24 |
| B63 | A20 | 8 | 2 | 24 | 9 | 2 | 24 |
| B64 | A21 | 5 | 2 | 24 | 8 | 2 | 24 |
| B65 | A22 | 8 | 2 | 24 | 9 | 2 | 24 |
| B66 | A23 | 9 | 2 | 24 | 9 | 2 | 24 |
| B67 | A24 | 7 | 2 | 24 | 9 | 2 | 24 |
| B68 | A25 | 5 | 2 | 24 | 8 | 2 | 24 |
| B69 | A26 | 8 | 3 | 24 | 8 | 3 | 24 |
| B70 | A27 | 4 | 2 | 24 | 7 | 2 | 24 |
| B71 | A85 | 8 | 3 | 24 | 9 | 3 | 24 |
| B72 | A29 | 9 | 3 | 24 | 10 | 3 | 24 |
| B73 | A97 | 6 | 2 | 24 | 8 | 2 | 24 |
| B74 | A30 | 9 | 3 | 24 | 10 | 3 | 24 |

What is claimed is:

1. A compound of the formula I

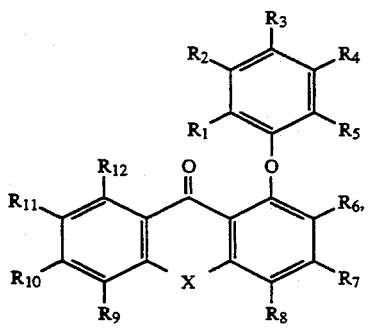

in which

X is O, S, SO, $SO_2$ or $NR_{13}$, $R_1$ to $R_5$, independently of one another, are H, $C_1$-$C_{12}$alkyl, $C_1$-$C_{12}$alkoxy, $C_1$-$C_{12}$alkylthio, $C_1$-$C_4$alkyl—SO—, $C_1$-$C_4$alkyl—$SO_2$—, halogen, $CF_3$, —CN, —$NO_2$, —OH, —$COOR_{14}$, —$CON(R_{15})_2$, or —$N(R_{15})_2$, or the radical of the formula

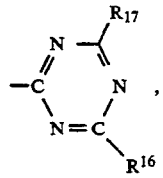

in which $R_{16}$ and $R_{17}$, independently of one another, are $C_1$-$C_6$alkyl, phenyl, $C_1$-$C_6$alkylphenyl or $(C_1$-$C_6$alkyl$)_2$-phenyl, or $R_3$ and $R_4$ or $R_4$ and $R_5$, in each case together, are —CH=CH—CH=CH—, $R_6$ to $R_{12}$, independently of one another, are H, $C_1$-$C_{12}$alkyl, $C_1$-$C_{12}$alkoxy, $C_1$-$C_{12}$alkylthio, $C_1$-$C_{12}$alkyl—SO—, $C_1$-$C_{12}$alkyl—$SO_2$—, benzyl or $C_1$-$C_4$.$_6$alk-1-yl which is 1-substituted by a total of one or two —CN and/or —$COOR_{14}$, phenyl, phenyl—$C_1$-$C_4$alkylene, phenyl—CO—, phenyloxy, phenylthio, phenyl—SO—, pnenyl—$SO_2$—, benzyloxy, benzylthio, benzyl—SO—, benzyl—$SO_2$—, $C_1$-$C_{18}$acyl—O—, —$COOR_{14}$, —$CON(R_{15})_2$, $C_1$-$C_{18}$acyl—$NR_{15}$—, $(R_{15})_2N$—, halogen, —$CF_3$ or —CN, or each two adjacent racicals of $R_6$ to $R_{12}$ are the groups —CO—O—CO— or —CO—$NR_{13}$—CO— the pheynyl radicals and radicals containing pnehyl groups being unsubstituted or substituted by halogen, —CN, —$CF_3$, $C_1$-$C_6$alkylthio, $C_1$-$C_6$alkoxy, $C_1$-$C_6$alkyl, —$COOR_{14}$, —CO—$N(R_{15})_2$ or $C_1$-$C_{12}$acyl—O—, $R_{13}$ is H, $C_1$-$C_{12}$alkyl or $C_1$-$C_{12}$acyl, phenyl or benzyl, which are unsubstituted or substituted by $C_1$-$C_6$alkyl, $C_1$-$C_6$alkoxy, $C_1$-$C_6$alkylthio, halogen or —$COOR_{14}$, the two $R_{15}$ together are $C_4$-$C_8$alkylene, 3-oxa-1,5-pentylene, 3-thia-1,5-pentylene, 1.3-butadiene-1,4-diyl or 2-aza-1,3-butadiene-1,4-diyl, or the $R_{15}$ radicals, independently of one another, are H, $C_1$-$C_{12}$alkyl, or phenyl or benzyl which is unsubstituted or substituted by $C_1$-$C_6$alkyl, $C_1$-$C_6$alkoxy, $C_1$-$C_6$alkylthio, halogen or —$COOR_{14}$, and $R_{14}$ is phenyl, $(C_1$-$C_4$alkyl$)$phenyl, benzyl, 1-phenyleth-2-yl, benzyl or 1-phenyleth-2-yl substituted by 1 or 2 $C_1$-$C_{12}$-alkyl, $C_1$-$C_{20}$-alkyl, $C_3$-$C_8$-cycloalkyl, $C_3$-$C_8$-cycloalkylmethyl, or a polyoxaalkylene radical of the formula —$(C_nH_{n2}$—O—$)_mR_{18}$, in which n is an integer from 2 to 4, m is a number from 1 to 12, and $R_{18}$ is $C_1$-$C_{18}$-alkyl, $C_{34}$-$C_8$-cycloalkyl, $C_5$- or $C_6$-cycloalkylmethyl, phenyl, benzyl, or phenyl or benzyl, substituted by 1 or 2 alkyl groups having 1 to 12 carbon atoms, with the exception of 1-phenoxy-4-methylxanthen-9-one.

2. A compound according to claim 1, in which, in the formula I, $R_1$ to $R_5$, independently of one another, are H, $C_1$-$C_6$alkyl, $C_1$-$C_6$alkoxy, halogen, —$CF_3$, —CN, —$NO_2$, —$COOR_{14}$, —OH, or —$N(R_{15})_2$, or $R_3$ and $R_4$ or $R_4$ and $R_5$, in each case together, are —CH=CH—CH=CH—, each $R_{15}$ is $C_1$-$C_6$alkyl, and $R_{14}$ is linear or branched $C_1$-$C_{18}$alkyl.

3. A compound according to claim 2, in which, in the formula I, at least 2 of the radicals $R_1$ to $R_5$ are H.

4. A compound according to claim 1, in which in the formula I $R_6$ to $R_{12}$, independently of one another, are H, $C_1$-$C_6$alkyl, $C_1$-$C_6$alkoxy, $C_1$-$C_6$alkylthio, $C_1$-$C_6$alkyl—SO—, $C_1$-$C_6$alkyl—$SO_2$, $C_1$- or $C_2$alkyl which is 1-substituted by a total of one or 2 —CN and/or COOR$_{14}$, phenyl, phenyl-C$_1$-C$_4$alkylene, phenyl—CO—, phenyloxy, phenylthio, phenyl—SO—, phenyl—SO$_2$—, benzyloxy, benzylthio, benzyl—SO—, benzyl—SO$_2$—, C$_1$-C$_8$acyl—NR$_{15}$—, —COOR$_{14}$, —CON(R$_{15}$)$_2$, (R$_{15}$)$_2$N—, —F, —Cl, —Br, —CF$_3$ or —CN or each two adjacent R$_6$ to R$_{12}$ radicals together are —CO—O—CO— or CO—NR$_{13}$—CO—, R$_{13}$ is C$_1$-C$_6$alkyl, or phenyl or benzyl which are unsubstituted or substituted by C$_1$-C$_4$alkyl, C$_1$-C$_4$alkoxy, F, Cl, Br or —COOR$_{14}$, R$_{14}$ is H, linear or branched C$_1$-C$_{18}$alkyl, phenyl, benzyl or —C$_n$H$_{2n}$—O$_m$R$_{18}$, where cyclohexyl, phenyl or benzyl, and R$_{15}$ is C$_1$-C$_6$alkyl, or phenyl or benzyl which is unsubstituted or substituted by C$_1$-C$_4$alkyl, C$_1$-C$_4$alkoxy, —F, —Cl, —Br or —COOR$_{14}$, or the two R$_{15}$ radicals together are 1,4-butylene, 1,5-pentylene, 3-oxa-1,5-pentylene or 1,3-butadiene-1,4-diyl.

5. A compound according to claim 1, in which, in the formula I at least two of the radicals R$_6$ to R$_{12}$ are H.

6. A compound according to claim 1, in which, in the formula I, R$_6$ is H, —Cl, —Br or methyl.

7. A compound according to claim 1, in which, in the formula I, R$_9$ is H or —Cl.

8. A compound according to claim 1, in which, in the formula I, R$_1$ is H or —Cl.

9. A compound according to claim 1, in which, in the formula I, R$_{10}$ and/or R$_{12}$ is —Cl, —Br, unsubstituted or substituted phenoxy or —COO—(C$_1$-C$_{12}$alkyl).

10. A compound according to claim 1, in which, in the formula I, R$_6$ is H, —Cl, —Br or methyl, or in which, in the formula I, R$_9$ is H or —Cl, or in which, in the formula I, R$_{11}$ is H or —Cl, or in which, in the formula I, R$_{10}$ and/or R$_{12}$ is —Cl, —Br, unsubstituted or substituted phenoxy or —COO—(C$_1$-C$_{12}$alkyl), or in which, in the formula I, R$_7$ and/or R$_8$ is H, —F, —Cl, —NO$_2$, —CR$_3$, —Br, C$_1$-C$_4$alkyl, C$_1$-C$_4$alkoxy, phenyl—CO—,α-cyanobenzyl, C$_1$-C$_8$acyl—NR$_{15}$—, pyrryl, —COO—(C$_1$-C$_{12}$alkyl), or phenoxy, phenylthio or phenylsulfonyl, which are unsubstituted or substituted by —F, —Cl, C$_1$-C$_4$alkyl, C$_1$-C$_4$alkoxy, —COOH or —COO—(C$_1$-C$_{12}$alkyl), or R$_7$ and R$_8$ together are

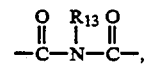

and R$_{13}$ is H or C$_1$-C$_6$alkyl.

11. A compound according to claim 1, in which, in the formula I, R$_{13}$ is C$_1$-C$_4$alkyl or C$_1$-C$_8$acyl, or phenyl or benzyl which are unsubstituted or substituted by F or —COOR$_{14}$, and R$_{14}$ is H or C$_1$-C$_{12}$alkyl.

12. A compound according to claim 1, in which, in the formula I, R$_{14}$ is H, C$_1$-C$_{18}$alkyl, —C$_n$H$_{2n}$—O$_m$H, phenyl, C$_1$-C$_6$alkylphenyl, benzyl, C$_1$-C$_6$alkylbenzyl or cyclohexyl, n is an integer from 1 to 6, and m is a number from 1 to 20.

13. A compound according to claim 1, in which, in the formula I, R$_{15}$ is H, C$_1$-C$_6$alkyl, phenyl, benzyl, or the two R$_{15}$ radicals together are tetramethylene, pentamethylene, 3-oxa-1,5-pentylene or 1,3-butadiene-1,4-diyl.

14. A compound according to claim 1, in which R$_1$ to r$_5$ are H or R$_1$, r$_2$, R$_4$ and R$_5$ are H and R$_3$ is —CO$_2$C$_2$H$_5$, R$_6$ and R$_8$ are Cl, and R$_7$ and R$_9$-R$_{12}$ are H and R$_3$ is —CO$_2$C$_2$H$_5$, R$_6$ and R$_8$ are Cl, and R$_7$ and R$_9$-R$_{12}$ are H, X is NCH$_3$ or N-n-C$_3$H$_7$.

15. The compound according to claim 9, wherein X is O, each of R$_1$ to R$_6$ and R$_8$ to R$_{11}$ are H, and R$_7$ and R$_{12}$ are phenoxy.

* * * * *